United States Patent [19]

Penco et al.

[11] 4,325,947
[45] Apr. 20, 1982

[54] 4-DEMETHOXY-4'-DEOXYDOXORUBICIN

[75] Inventors: Sergio Penco, Milan; Giuliano Franchi, Corsico; Federico Arcamone, Nerviano; Annamaria Casazza, Milan, all of Italy

[73] Assignee: Farmitalia Carlo Erba S.p.A., Milan, Italy

[21] Appl. No.: 263,002

[22] Filed: May 12, 1981

[51] Int. Cl.³ .................... A61K 31/70; C07H 15/24
[52] U.S. Cl. ................................. 424/180; 536/17 A
[58] Field of Search ...................... 424/180; 536/17 A

[56] References Cited
U.S. PATENT DOCUMENTS
4,067,969  1/1978  Penco et al. ...................... 536/17 A Primary Examiner—Johnnie R. Brown Attorney, Agent, or Firm—Oblon, Fisher, Spivak, McClelland & Maier

[57] ABSTRACT

A new anthracycline glycoside, which is 4-demethoxy-4'-deoxydoxorubicin, provided with outstanding antitumoral activity also by oral route, has been prepared by condensation of 4-demethoxydaunomycinone with 2,3,4,6-tetradeoxy-3-trifluoroacetamido-L-threo-hexopyranosyl chloride.

By elimination of the protecting group from the so obtained glycoside through a mild alkaline hydrolysis, 4-demethoxy-4'-deoxydaunorubicin was obtained which was successively brominated to give the corresponding 14-bromo derivative. By a subsequent hydrolysis with sodium formate the brominated intermediate was transformed into 4-demethoxy-4'-deoxydoxorubicin eventually isolated as its hydrochloride.

4 Claims, No Drawings

4,325,948

COMBATING PESTS WITH 2-CYCLOALKYL-PYRIMIDIN-5-YL-(THIONO) (THIOL)-PHOSPHORIC (PHOSPHONIC) ACID ESTERS AND ESTER-AMIDES

The present invention relates to and has for its objects the provision of particular new 2-cycloalkyl-pyrimidin-5-yl-(thiono)(thiol)-phosphoric (phosphonic) acid esters and ester-amides, which possess insecticidal, acaricidal and nematicidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

It is known that certain 2,6-dialkyl-pyrimidin-4-yl-thiono(thiol)-phosphoric acid esters, for example O,O-diethyl-O-(2-iso-propyl-6-methyl-pyrimidin-4-yl)thiono-phosphoric acid ester and O-ethyl-S-n-propyl-O-(2-iso-propyl-6-mehyl-pyrimidin-4-yl)-thionothiolphosphoric acid ester, are insecticidally and acaricidally active (see German Patent Specification No. 910,652 and U.S. Pat. No. 3,951,975.

However, the action of these compounds is not always satisfactory, especially if low amounts and low concentrations are used.

The present invention now provides, as new compounds, the 2-cycloalkyl-pyrimidin-5-yl-(thiono)(thiol)-phosphoric (phosponic) acid esters and ester-amides of the general formula $$R^3-\underset{N}{\overset{N}{\diagup}}\hspace{-2pt}\diagdown\hspace{-2pt}\underset{R^2}{\diagdown}-O-\underset{R^1}{\overset{X}{\overset{\|}{P}}}\diagup^{OR} \quad (I)$$

in which
R represents alkyl,
$R^1$ represents alkyl, alkoxy, alkylthio, alkylamino or phenyl,
$R^2$ represents hydrogen or alkyl,
$R^3$ represents cycloalkyl and
X represents oxygen or sulphur.
Preferably, in formula (I),
R represents straight-chain or branched alkyl with 1 to 5 (especially 1 to 3) carbon atoms,
$R^1$ represents straight-chain or branched alkyl with 1 to 5 (especially 1 to 3) carbon atoms, straight-chain or branched alkoxy, alkylthio or alkylamino, in each case with 1 to 5 (especially 1 to 3) carbon atoms per alkyl radical, or phenyl,
X represents oxygen or sulphur,
$R^2$ represents hydrogen or methyl, and
$R^3$ represents cycloalkyl with 3 to 6 carbon atoms.

Surprisingly, the 2-cycloalkyl-pyrimidin-5-yl-(thiono)(thiol)-phosphoric(phosphonic) acid esters and ester-amides according to the invention exhibit a better insecticidal, acaricidal and nematicidal action than the corresponding compounds, known from the prior art, of analogous structure and of the same type of action.

The invention also provides a process for the preparation of a 2-cycloalkylpyrimidin-5-yl-(thiono)(thiol)-phosphoric(phosphonic) acid ester or ester-amide of the formula (I), in which a (thiono)(thiol)-phosphoric(phosphonic) acid ester halide or (thiono)phosphoric acid ester-amide halide of the general formula $$Hal-\underset{R^1}{\overset{X}{\overset{\|}{P}}}\diagup^{OR} \quad (II)$$

in which
R, $R^1$ and X have the above-mentioned meanings and
Hal represents chlorine or bromine,
is reacted with a 5-hydroxy-pyrimidine of the general formula $$R^3-\underset{N}{\overset{N}{\diagup}}\hspace{-2pt}\diagdown\hspace{-2pt}\underset{R^2}{\diagdown}-OH, \quad (III)$$

in which
$R^2$ and $R^3$ have the above-mentioned meanings,
if appropriate in the presence of an acid acceptor and, if appropriate, in the presence of an inert diluent.

If, for example, 2-cyclobutyl-5-hydroxypyrimidine and O-ethyl-ethanephosphonic acid ester chloride are used as starting materials, the reaction can be outlined by the following equation:

$$\underset{N}{\overset{N}{\diagup}}\hspace{-2pt}\diagdown\hspace{-2pt}-OH + Cl-\underset{C_2H_5}{\overset{O}{\overset{\|}{P}}}\diagup^{OC_2H_5} \xrightarrow{-HCl}$$

$$\underset{N}{\overset{N}{\diagup}}\hspace{-2pt}\diagdown\hspace{-2pt}-O-\underset{C_2H_5}{\overset{O}{\overset{\|}{P}}}\diagup^{OC_2H_5}$$

The (thiono)(thiol)-phosphoric(phosphonic) acid ester halides and (thiono)-phosphoric acid ester-amide halides to be used as starting materials, are defined by the formula (II).

Preferably in this formula, R, $R^1$ and X have the meanings stated to be preferred in connection with the formula (I) and Hal represents chlorine.

The (thiono)(thiol)-phosphoric(phosphonic) acid ester halides and (thiono)-phosphoric acid ester-amide halides of the formula (II) are known compounds. The following may be mentioned as examples: O-methyl-, O-ethyl-, O-n-propyl-, O-iso-propyl-methane-, -ethane-, -propane- and -phenyl-phosphonic acid ester chloride and the corresponding thiono analogues; O,O-dimethyl-, O,O-diethyl-, O,O-di-n-propyl, O-methyl-O-ethyl-, O-methyl-O-n-propyl, O-methyl-O-iso-propyl, O-ethyl-O-n-propyl- and O-ethyl-O-iso-propyl-phosphoric acid diester chloride and the corresponding thiono analogues; O,S-dimethyl-, O,S-diethyl-, O,S-di-n-propyl-, O,S-di-iso-propyl-, O-ethyl-S-n-propyl-, O-ethyl-S-iso-propyl-, O-ethyl-S-sec.-butyl-, O-n-propyl-S-ethyl-, O-n-propyl-S-iso-propyl- and O-iso-propyl-S-n-propyl-thiolphosphoric acid diester chloride and the corresponding thiono analogues; and O-methyl-N-methyl-, O-methyl-N-ethyl-, O-methyl-N-propyl-, O-methyl-N-iso-propyl, O-ethyl-N-methyl-, O-ethyl-N-ethyl-, O-ethyl-N-n-propyl-, O-ethyl-N-iso-propyl-, O-n-propyloral route (Table 4). In summary, XOO-0144 in comparison with doxorubicin is:

(1) more potent in vitro
(2) more potent in vivo (both i.p. and i.v. administration)
(3) more active against L1210 leukemia
(4) active also when administered orally.

TABLE 1

Activity on HeLa cells cloning efficiency in vitro. Treatment for 24 hours.

| Compound | Dose (ng/ml) | % of controls | $ID_{50}$ (ng/ml) |
|---|---|---|---|
| Doxorubicin | 12.5 | 44 | ~10 |
|  | 6.2 | 68 |  |
|  | 3.1 | 102 |  |
| XOO-0144 | 25 | 0 | ~0.4 |
|  | 6.2 | 1 |  |
|  | 1.5 | 26 |  |
|  | 0.39 | 69 |  |
|  | 0.09 | 72 |  |
|  | 0.02 | 102 |  |

TABLE 2

Activity against P388 ascitic leukemia[1]

| Compound | Dose[2] (mg/kg) | T/C[3] % | Toxic deaths |
|---|---|---|---|
| Doxorubicin | 4.4 | 210, 180 | 0/16 |
|  | 6.6 | 220, 190 | 0/16 |
|  | 10.0 | 225, 220 | 0/16 |
| XOO-0144 | 0.04 | 130 |  |
|  | 0.12 | 170 |  |
|  | 0.25 | 205, 195 |  |
|  | 0.5 | 235 |  |
|  | 1 | 75, 90 | 7/16 |
|  | 5 | 55 | 8/8 |

[1]Mice were injected ip with $10^6$ leukemia cells/mouse. Data of 2 experiments.
[2]Treatment ip on day 1 after tumor inoculum.
[3]Medium survival time of treated animals/medium survival time of controls × 100.

TABLE 3

Activity against disseminated L1210 leukemia[1].

| Compound | Dose[2] (mg/kg) | T/C[3] % | Toxic deaths |
|---|---|---|---|
| Doxorubicin | 10 | 133 | 0/10 |
|  | 13 | 150 | 0/9 |
|  | 16.9 | 166 | 1/10 |
| XOO-0144 | 0.9 | 183 | 0/10 |
|  | 1.2 | 191 | 0/10 |
|  | 1.56 | 116 | 6/10 |

[1]CDF-1 female mice were injected iv with $10^5$ leukemia cells/mouse.
[2]Treatment iv on day 1 after tumor inoculum.
[3]Medium survival time of treated animals/medium survival time of controls × 100

TABLE 4

Activity against Gross leukemia[1].

| Compound | Route | Dose[2] (mg/kg) | T/C[3] % | Toxic deaths |
|---|---|---|---|---|
| Doxorubicin | i.v. | 13 | 200, 200 | 0/18 |
|  |  | 16.9 | 233, 216 | 0/18 |
| XOO-0144 | i.v. | 0.35 | 100 | 0/8 |
|  |  | 0.53 | 108 | 0/8 |
|  |  | 0.8 | 116 | 0/10 |
|  |  | 1.2 | 150, 208 | 0/20 |
|  |  | 1.8 | 133 | 9/10 |
|  |  | 2.7 | 116 | 10/10 |
|  | oral | 2.7 | 150 | 1/8 |
|  |  | 5.4 | 133 | 4/6 |
|  |  | 10.8 | 100 | 5/5 |

[1]C3H female mice were injected iv with 2 × $10^6$ leukemia cells/mouse. Data of 2 experiments.
[2]Treatment on day 1 after tumor inoculum.
[3]Medium survival time of treated animals/medium survival time of controls × 100.

What we claim is:
1. A compound of general formula I:

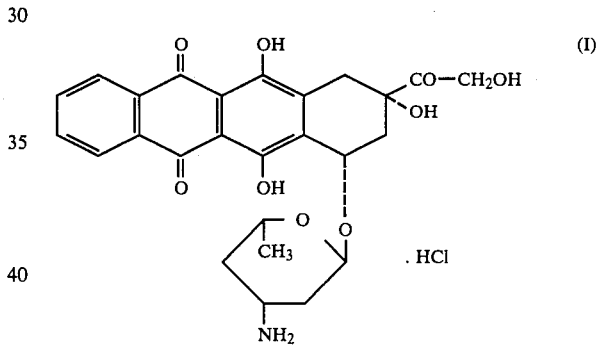

which is 4-demethoxy-4'-deoxydoxorubicin hydrochloride.

2. A method of inhibiting the growth of a tumor selected from the group consisting of $L_{1210}$ leukemia, transplanted Gross leukemia and lymphocitic $P_{388}$ leukemia which comprises administering to a host afflicted with said tumors an amount of a compound according to claim 1 sufficient to inhibit the growth of said tumors.

3. A method according to claim 2, wherein said compound is administered intraperitoneally intravenously or by oral route.

4. A pharmaceutical composition comprising a therapeutically effective amount of a compound as claimed in claim 1 and an inert carrier thereof.

* * * * * from the order of the Isoptera, for example Reticulitermes spp.;

from the order of the Anoplura, for example *Phylloxera vastatrix*, Pemphigus spp., *Pediculus humanus corporis*, Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Climex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus supp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus supp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hopolocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp., The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefield gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules or inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an exellent residual activity on wood and clay as well as a good stability to alkali on limed substrates.

The 2-cycloalkyl-pyrimidin-5-yl-(thiono)(thiol)phosphoric(phosphonic) acid esters and ester-amides also have a good root-systemic action against sucking and biting insects and mites.

The present invention also provides an arthropodicidal or nematicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) or nematodes which comprises applying to the arthropods or nematodes, or to a habitat thereof, a compound of the present invention alone or in the form of a composition containing as active ingredient a compound of the present invention in admixture with a diluent or carrier.

The present invention further provides crops protected from damage by arthropods or nematodes by being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the novel compounds is shown in the following illustrative example:

EXAMPLE 1

(a) The 5-hydroxy-pyrimidines to be employed as starting materials could be prepared, for example, as follows:

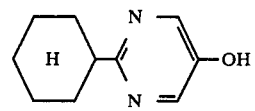

83.8 g (0.65 mol) of 2-methoxy-3-dimethylaminoacrolein (for preparation see H. Plumpe and E. Schegk, Archiv der Pharmazie 300, (1967) pages 704–708) were added at room temperature to a mixture of 116.2 g (0.72 mol) of cyclohexylamidine hydrochloride, 150 ml of methanol and 0.8 mol of a solution of sodium methylate in methanol. The mixture was boiled for 5 hours under reflux and cooled to room temperature, and the salt which had precipitated was filtered off. It was rinsed with 100 ml of methanol, a solution of 56 g (1 mol) of potassium hydroxide in 100 ml of water was added to the filtrate and the solution was then heated in an autoclave for 4 hours to 190° C. The methanol was then distilled off in vacuo, 50 ml of ice water were added to the residue and the solution was brought to a pH value of 4.5 by adding concentrated hydrochloric acid, while cooling. After 30 minutes, the product which had crystallized out was filtered off and 96 g (83% of theory) of 2-cyclohexyl-5-hydroxy-pyrimidine were thus obtained as a pale brown-colored crystal powder of melting point 163° C.

The following compounds of the formula

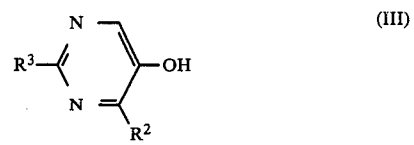

could be prepared analogously:

| Intermediate | $R^2$ | $R^3$ | Yield (% of theory) | Melting point (°C.) |
|---|---|---|---|---|
| b | H | △ | 85 | 187 |
| c | H | □ | | |
| d | H | ⬠ | 67 | 220 |
| e | $CH_3$ | △ | | |

(b)

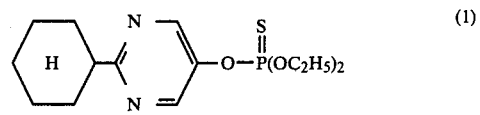

A mixture of 300 ml of acetonitrile, 17.8 g (0.1 mol) of 2-cyclohexyl-5-hydroxy-pyrimidine, 20.7 g (0.15 mol) of potassium carbonate and 18.8 g (0.1 mol) of O,O-diethylthionophosphoric acid diester chloride was stirred for 2 hours at 45° C. The reaction mixture was then poured into 400 ml of toluene and was washed with twice 300 ml of water. The toluene solution was dried over sodium sulphate and evaporated in vacuo. The residue was subjected to incipient distillation in a high vacuum. This gave 21.7 g (66% of theory) of O,O-diethyl-O-(2-cyclohexyl-pyrimidin-5-yl)-thionophosphoric acid ester in the form of a brown oil of refractive infex $n_D^{23}$: 1.5158.

The following compounds of the formula

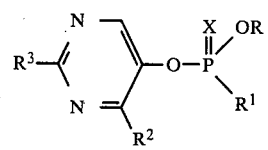

could be prepared analogously:

TABLE 2

| Compound No. | R | $R^1$ | $R^2$ | $R^3$ | X | Yield (% of theory) | Physical data (Refractive index; melting point °C.) |
|---|---|---|---|---|---|---|---|
| 2 | $C_2H_5$ | $NH-C_3H_7-iso$ | H | ⟨H⟩ hexyl | S | 51 | $n_D^{23}$:1.5246 |
| 3 | $CH_3$ | $OCH_3$ | H | ⟨H⟩ hexyl | S | 64 | $n_D^{23}$:1.5287 |
| 4 | $C_2H_5$ | $OC_2H_5$ | H | cyclopropyl | S | 78 | $n_D^{24}$:1.5142 |
| 5 | $C_2H_5$ | $NH-C_3H_7-iso$ | H | cyclopropyl | S | 62 | 49 |
| 6 | $CH_3$ | $OCH_3$ | H | cyclopropyl | S | 43 | $n_D^{24}$:1.5390 |
| 7 | $C_3H_7-n$ | $OC_2H_5$ | H | cyclopropyl | S | 71 | $n_D^{25}$:1.5128 |
| 8 | $C_2H_5$ | $NH-C_2H_5$ | H | cyclopropyl | S | 74 | $n_D^{26}$:1.5310 |
| 9 | $C_2H_5$ | $OC_2H_5$ | H | cyclobutyl | S | | |
| 10 | $C_2H_5$ | $OC_2H_5$ | $CH_3$ | cyclopropyl | S | | |
| 11 | $C_2H_5$ | $OC_2H_5$ | H | ⟨H⟩ pentyl | S | 80 | $n_D^{23}$:1.5164 |
| 12 | $C_2H_5$ | $OC_3H_7-n$ | H | ⟨H⟩ pentyl | S | | |
| 13 | $C_2H_5$ | $CH_3$ | H | cyclopropyl | S | 72 | $n_D^{25}$:1.5428 |
| 14 | $C_2H_5$ | $OC_2H_5$ | H | cyclopropyl | O | | |
| 15 | $C_2H_5$ | $NH-C_3H_7-iso$ | H | cyclopropyl | O | | |
| 16 | $C_2H_5$ | phenyl | H | cyclopropyl | S | 74 | $n_d^{25}$:1.5815 |
| 17 | $C_2H_5$ | $SC_3H_7-n$ | H | cyclopropyl | S | | |
| 18 | $C_2H_5$ | phenyl | H | ⟨H⟩ hexyl | S | | |
| 19 | $C_2H_5$ | $NH-C_2H_5$ | H | ⟨H⟩ hexyl | S | 66 | $n_D^{23}$:1.5329 |
| 20 | $C_2H_5$ | $SC_3H_7-n$ | H | cyclopropyl | O | | |
| 21 | $C_2H_5$ | $C_2H_5$ | H | cyclopropyl | S | | |
| 22 | $CH_3$ | $C_2H_5$ | H | cyclopropyl | S | | |
| 23 | $C_3H_7-iso$ | $CH_3$ | H | cyclopropyl | S | 67 | $n_D^{26}$:1.5233 |
| 24 | $CH_3$ | $NH-C_3H_7-iso$ | H | cyclopropyl | S | | |

TABLE 2-continued

| Compound No. | R | R¹ | R² | R³ | X | Yield (% of theory) | Physical data (Refractive index; melting point °C.) |
|---|---|---|---|---|---|---|---|
| 25 | $CH_3$ | $NH-CH_3$ | H |  | S | 66 | $n_D^{26}$:1.5460 |
| 26 | $C_2H_5$ | $NH-CH_3$ | H |  | S | | |
| 27 | $CH_3$ | $NH-C_2H_5$ | H |  | S | | |
| 28 | $C_2H_5$ | $NH-C_3H_7-iso$ | H |  | S | 55 | $n_D^{23}$:1.5247 |

The pesticidal activity of the compounds of this invention is illustrated by the following examples wherein the compounds according to the present invention are each identified by the number (given in brackets) from Example 1:

EXAMPLE 2

Test insect: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (=mg/l). The treated soil was filled into pots and the pots were left to stand at room temperature.

After 24 hours the test insects were introduced into the treated soil and after a further 2 to 7 days the degree of effectiveness of the active compound was determned in % by counting the dead and the live test insects. The degree of effectiveness was 100% if all of the test insects had been killed and was 0% if exactly as many test insects were still alive as in the case of the untreated control.

In this test, for example, the following compounds showed a superior action compared to the prior art: (7) and (16).

EXAMPLE 3

Test insect: *Tenebric molitor* larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (=mg/l). The treated soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all of the test insects had been killed and was 0% if exactly as many test insects were still alive as in the case of the untreated control.

In this test, for example, the following compounds showed a superior action compared to the prior art: (1), (4) and (7).

EXAMPLE 4

Test insect: *Myzus persicae*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added to the desired concentration.

The preparation of active compound was intimately mixed with the soil. The concentration of the active compound in the preparation was of practically no importance; only the amount of active compound per unit volume of soil, which is given hereinafter in ppm (=mg/l), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the above-mentioned test insects after 7 days. After a further 2 days, the results were evaluated by counting or estimating the dead insects. The root-systemic action of the active compound was deduced from the destruction data. It was 100% when all of the test insects had been killed and 0% when just as many test insects were still alive as in the case of the untreated control.

In this test, for example, the following compounds showed a superior action compared to the prior art: (4) and (5).

EXAMPLE 5

Test insect: *Phaedon cochleariae* larvae
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm (=mg/l), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the above-mentioned test insects after 7 days. After a further 2 days, the results were evaluated by counting or estimating the dead insects. The root-systemic action of the active compound was deduced from the destruction data. It was 100% when all of the test insects had been killed and 0% when just as many test insects were still alive as in the case of the untreated control.

In this test, for example, the following compounds showed a superior action compared to the prior art: (4) and (5).

EXAMPLE 6

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given hereinafter in ppm (=mg/l), was decisive. The treated soil was filled into pots, lettuce was sown in and the pots were kept at a greenhouse temperature of 27 degrees C.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

In this test, for example, the following compounds showed a superior activity compared to the prior art: (4) and (5).

EXAMPLE 7

Test insects: *Sitophilus granarius*
Number of test animals: 25
Solvent: Acetone The active compound was taken up in the solvent at a rate of 2 g per liter. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. The stated number of test insects was then placed in the Petri dish and the dish was covered with a glass lid.

The condition of the test insects was observed 3 days after the commencement of the experiments. The destruction, in %, was determined. 100% denoted that all of the test insects had been killed; 0% denoted that none of the test insects had been killed.

In this test, for example, the following compounds showed a superior action compared to the prior art: (4) and (6).

EXAMPLE 8

Laphygma test
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Cabbage leaves (*Brassica oleracea*) were treated by being dipped into the preparation of active compound of the desired concentration and were infested with caterpillars of the owlet moth (*Laphygma frugiperda*), as long as the leaves were still moist.

After the specified periods of time, the destruction in % was determined. 100% meant that all of the caterpillars had been killed whereas 0% indicated that none of the caterpillars had been killed.

In this test, for example, the following compounds showed a superior activity compared to the prior art: (13), (4), (1), (7) and (16).

EXAMPLE 9

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were treated by being dipped into the preparation of the active compound of the desired concentration.

After the specified periods of time, the degree of destruction was determined as a percentage: 100% meant that all of the spider mites were killed whereas 0% meant that none of the spider mites were killed.

In this test, for example, the following compounds showed a superior activity compared to the prior art: (13), (4), (7) and (5).

It will be appreciated that the instant specification and examples are set forth by way of illustration and not limitation, and that various modifications and changes may be made without departing from the spirit and scope of the present invention.

What is claimed is:

1. A 2-cycloalkyl-pyrimidin-5-yl-(thiono)(thiol)-phosphoric (phosphonic) aced ester or ester-amide of the formula

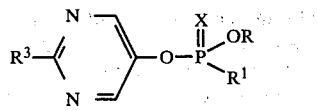

in which
R is alkyl with 1 to 5 carbon atoms,
$R^1$ is alkyl, alkoxy, alkylthio or alkylamino each with 1 to 5 carbon atoms per alkyl radical, or phenyl,
$R^3$ is cycloalkyl with 3 to 6 carbon atoms, and
X is oxygen or sulphur.

2. A compound according to claim 1, in which $R^3$ is cyclopropyl.

3. A compound according to claim 1, wherein such compound is O,O-diethyl-O-(2-cyclohexyl-pyrimidin-5-yl)-thionophosphoric acid ester of the formula

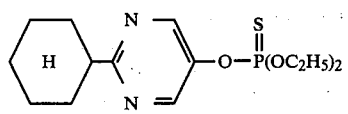

4. A compound according to claim 1, wherein such compound is O,O-diethyl-O-(2-cyclopropyl-pyrimidin-5-yl)-thionophosphoric acid ester of the formula

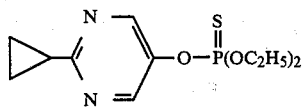

5. A compound according to claim 1, wherein such compound is O-ethyl-O-n-propyl-O-(2-cyclopropyl-pyrimidin-5-yl)-thionophosphoric acid ester of the formula

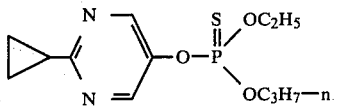

6. A compound according to claim 1, wherein such compound is O-ethyl-O-(2-cyclopropyl-pyrimidin-5-yl)-phenylthionophosphonic acid ester of the formula

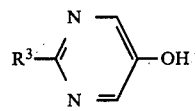

7. An arthropodicidal or nematicidal composition containing as active ingredient an arthropodicidally or nematicidally effective amount of a compound according to claim 1 in admixture with a diluent.

8. A method of combating arthropods or nematodes which comprises applying to the arthropods or nematodes, or to a habitat thereof, an arthropodicidally or nematidially effective amount of a compound according to claim 1.

9. The method according to claim 8, in which said compound is
O,O-diethyl-O-(2-cyclohexyl-pyrimidin-5-yl)-thionophosphoric acid ester,
O,O-diethyl-O-(2-cyclopropyl-pyrimidin-5-yl)-thionophosphoric acid ester,
O-ethyl-O-n-propyl-O-(2-cyclopropyl-pyrimidin-5-yl)-thionophosphoric acid ester, or
O-ethyl-O-(2-cyclopropyl-pyrimidin-5-yl)-phenylthionophosphonic acid ester.

10. A compound of the formula wherein $R^3$ is cycloalkyl of 3 to 6 carbon atoms.

* * * * *